(12) United States Patent
Berg (10) Patent No.: US 10,750,751 B2
(45) Date of Patent: Aug. 25, 2020

(54) HONEY BASED BIOCIDE COMPOSITION

(71) Applicant: Charles Russell Berg, Medford, OR (US)

(72) Inventor: Charles Russell Berg, Medford, OR (US)

( * ) Notice: Subject to any disclaimer, the term of this patent is extended or adjusted under 35 U.S.C. 154(b) by 259 days.

(21) Appl. No.: 16/059,351

(22) Filed: Aug. 9, 2018

(65) Prior Publication Data

US 2018/0343874 A1    Dec. 6, 2018

Related U.S. Application Data

(62) Division of application No. 14/798,229, filed on Jul. 13, 2015, now Pat. No. 10,201,163.

(60) Provisional application No. 62/102,929, filed on Jan. 13, 2015.

(51) Int. Cl.

| A01N 63/02 | (2006.01) |
|---|---|
| A01N 25/30 | (2006.01) |
| A01N 25/12 | (2006.01) |
| A61K 35/644 | (2015.01) |
| A01N 63/10 | (2020.01) |
| A61K 31/616 | (2006.01) |
| A01N 37/40 | (2006.01) |
| A23L 3/3463 | (2006.01) |

(52) U.S. Cl.
CPC .............. *A01N 63/10* (2020.01); *A01N 25/12* (2013.01); *A01N 25/30* (2013.01); *A01N 37/40* (2013.01); *A23L 3/3463* (2013.01); *A61K 31/616* (2013.01); *A61K 35/644* (2013.01); *A23V 2002/00* (2013.01)

(58) Field of Classification Search
CPC .............. A61K 2300/00; A61K 35/644; A61K 31/616; A01N 37/40; A01N 59/00; A01N 63/02; A01N 63/10; A01N 65/00; A01N 25/02; A01N 25/12; A01N 25/30; A61Q 17/005; A23L 3/3463; A23V 2002/00
See application file for complete search history.

(56) References Cited

U.S. PATENT DOCUMENTS

| 1,989,981 A | 2/1935 | Hamilton |
| 2,191,259 A | 2/1940 | Pfaff et al. |
| 2,921,881 A | 1/1960 | Lamb |
| 3,065,135 A | 11/1962 | Hamptschein |
| 4,386,071 A | 5/1983 | Carle |
| 4,849,216 A | 7/1989 | Andersen |
| 5,186,935 A | 2/1993 | Tucker |

FOREIGN PATENT DOCUMENTS

| CN | 103651576 | 3/2014 |
| WO | WO2011057421 | 5/2011 |

OTHER PUBLICATIONS

Kwakman PHS, te Veide AA, de Boer L, Vandenbroucke-Grauls CMJE, Zaat SAJ "Two Major Medicinal Honeys Have Different Mechanisms of Bactericidal Activity" PLoS ONE, Mar. 4, 2001, 6(3): e17709, 7 pages. doi: 10.137/journal.pone.0017709. (Year 2011).

*Primary Examiner* — Aaron J Kosar
(74) *Attorney, Agent, or Firm* — Jerry Haynes Law (57) ABSTRACT

A biocide composition that provides an organic and food grade biocide to serve as an insecticide, moldicide and fungicide. The biocide composition consists of honey; acetylsalicylic acid; polysaccharide; guar gum; bee propolis; decylglucoside; and water. The crystallization of the honey is central to the effectiveness of the biocide composition. The biocide composition is safe, 100% organic, environmentally friendly, and pesticide free. Thus, the biocide composition enables a process of keeping infestations under control without the use of dangerous chemicals. The composition is formulated through generally known analytical chemistry that includes a series of mixing, heating, crystallization, dilutions, and finally liquefying into a usable form for dispersion. The biocide composition kills rapidly and leaves a protective barrier behind when applied in a mist to the walls and surfaces of the plant.

20 Claims, 9 Drawing Sheets

|  | INGREDIENT | AMOUNT |
|---|---|---|
| 102 | HONEY | 1 PINT |
| 104 | ACETYLSALICYLIC ACID | 645 MILLIGRAMS |
| 106 | POLYSACCHARIDE | 1 PINT |
| 108 | GUAR GUM | 1/8 OUNCE |
| 110 | BEE PROPOLIS (1%) | 1 TEASPOON |
| 112 | DECYL GLUCOSIDE | ½ OUNCE |
| 114 | WATER | 1 GALLON |

HONEY BASED BIOCIDE COMPOSITION

CROSS-REFERENCE TO RELATED APPLICATIONS

This application is a divisional application of U.S. application Ser. No. 14/798,229, entitled "Honey Based Biocide Composition", filed Jul. 13, 2015, which application claims priority from U.S. Provisional Application No. 62/102,929, entitled "Honey Based Biocide Composition", filed Jan. 13, 2015, which applications are hereby incorporated herein by reference in their entirety.

FIELD OF THE INVENTION

The present invention relates generally to a honey based biocide composition and more particularly the present invention relates to a biocide composition consisting of honey, crystallized forms of honey, and other natural ingredients that form organic 3-in-1 biocide comprising insecticides, moldicides, and fungicides.

BACKGROUND OF THE INVENTION

Biocide is an active chemical molecule to control the growth of or kill bacteria. Conventional biocides available have several drawbacks. One type of biocide has oxidizing action to either kill the bacteria and fungi outright, or it weakens the cell walls so that they are more susceptible to the other main class of biocides. The other type of biocide involves highly toxic organic chemicals. Subclasses of toxic biocides are generally known as thiazoles, thiocyanates, isothiazolins, cyanobutane, dithiocarbamate, thione, and bromo-compounds.

In order to overcome the above drawbacks, the present invention uses crystallized honey as an essential ingredient to obtain an organic, food grade biocide that chiefly kills small insects and controls contamination and the growth of molds and mildews.

The purpose of the present invention is to provide an organic, food grade, three in one biocide that serves as an insecticide, moldicide, and fungicide. The generally organic nature of the ingredients that makes up the biocide composition results in a safe, purely organic, environmentally friendly, and pesticide free biocide. The present invention enables a process of keeping infestations under control without the use of dangerous chemicals, thus it may be used on plants and in proximity of food. Further it requires few costly ingredients or sophisticated laboratory equipment.

Numerous innovations for biocides have been provided as described below. Even though these innovations may be suitable for the specific purposes to which they address, they differ significantly from the present invention however.

U.S. Pat. No. 1,989,981, to Hamilton, teaches an insecticide compound especially useful for killing ants containing an ant poison including sugar, honey, a thallium compound, agar, and water. Hamilton does not, however, teach an organic 3-in-1 biocide that can act as insecticide, moldicide, and fungicide. Also it does not describe a biocide composition consisting of crystallized forms of honey, and other natural ingredients and several other advantages and improvement of the present invention.

U.S. Pat. No. 2,191,259 to Pfaff et al., teaches an insecticide comprising an inert substance and a diazoamino compound free from sulfonic acid groups and carboxyl groups, however, Pfaff et al. does not teach an organic 3-in-1 biocide composition consisting of crystallized forms of honey and other natural ingredients that can act as insecticide, moldicide, and fungicide and several other advantages and improvement of the present invention.

U.S. Pat. No. 5,186,935 to Tucker describes an insecticidal composition based on diatomaceous silica. But Tucker fails to disclose a biocide composition consisting of crystallized forms of honey and other natural ingredients that can act as insecticide, moldicide, and fungicide and several other advantages and improvement of the present invention.

WIPO published application WO2011057421A3 to Pontifica Universidad, teaches a phenolic extract honey to serves as a disinfectant and sanitizer for sanitary and domestic use, as well as for topical or systemic application as a bactericide and fungicide in living beings. Pontifica Universidad does not, however, disclose a biocide composition consisting of crystallized forms of honey and other natural ingredients that can act as insecticide, moldicide, and fungicide and several other advantages and improvement of the present invention.

It is apparent that numerous innovations for biocides such as insecticides or moldicides or fungicides have been provided that are adequate for various purposes. Even though these innovations may be suitable for the specific purposes to which they address, they would not be suitable for the purposes of the present invention as heretofore described. Thus an organic, food grade, three in one biocide that serves as an insecticide, moldicide, and fungicide is needed.

SUMMARY OF THE INVENTION

The present invention discloses about a biocide composition containing crystallized forms of honey and further the composition provides an organic, food grade biocide that serves as an insecticide, moldicide, and fungicide.

The saturated crystal form of the biocide enhances the performance of the composition, wherein the biocide composition comprising the decylglucoside which acts as a surfactant to suspend the crystals in an air-water solution, when applied to a surface the dilute crystals will float along the surface of the surfactant and concentrate, i.e., super saturate, and become a chain of polymers that kills microorganisms and small insects, further upon drying, the biocide composition forms a protective surface of natural, long chain polymers and crystals that prevent growth of molds, fungus, bacteria, and acts as a disinfectant and antibacterial agent.

It is an object of the present invention to prepare a honey based biocide composition, wherein the composition comprising honey, acetylsalicylic acid, polysaccharide, guar gum, bee propolis, decylglucoside, and water.

It is another object of the present invention to provide a method for preparing a honey based biocide composition, the method comprising preparing a first solution by mixing acetylsalicylic acid with honey, wherein the first solution is vibrated until crystals are visible; preparing a second solution by mixing the crystals with the polysaccharide, wherein the second solution is blended into an aerated mixture to form supersaturated crystals, and then chilled; and preparing a third solution by mixing the supersaturated crystals with acetylsalicylic acid, decylglucoside, and water, wherein the third solution is mixed with guar gum and bee propolis to prepare the biocide composition.

It is still another object of the present invention to provide a method for preparing a honey based biocide composition, the method comprising preparing a first solution by mixing 325 milligrams of acetylsalicylic acid with 1 pint of honey, wherein the first solution is vibrated at about 10,000 Hz until crystals are visible; preparing a second solution by mixing 2 ounces of the crystals with one pint of the polysaccharide, wherein the second solution is blended into an aerated mixture to form supersaturated crystals, and then chilled at about 40° Fahrenheit for 48 hours; and preparing a third solution by mixing 2 ounces of the supersaturated crystals with 320 milligrams of acetylsalicylic acid, ½ ounce of decylglucoside, and 1 gallon of water, wherein the third solution is mixed with ⅛ ounce guar gum and one teaspoon of 1% concentration of bee propolis to prepare the biocide composition, wherein the saturated crystal form of the biocide enhance the performance of the composition, wherein the biocide composition comprising the decylglucoside which acts as a surfactant to suspends the crystals in an air-water solution, when applied to a surface the dilute crystals will float along the surface of the surfactant and concentrate, i.e., super saturate, and become a chain of polymers that kills micro-organisms and small insects, further upon drying, the biocide composition forms a protective surface of natural, long chain polymers and crystals that prevent growth of molds, fungus, bacteria, and acts as a disinfectant and antibacterial agent.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The invention will now be described, by way of example, with reference to the accompanying drawings, in which:

FIG. 1 illustrates a table of exemplary ingredients for a honey based biocide composition, in accordance with an embodiment of the present invention;

FIG. 2 illustrates an exemplary honey crystal, in accordance with an embodiment of the present invention;

FIGS. 3A and 3B illustrate the formation of crystals with an exemplary ultrasonic rod, where FIG. 3A shows crystals forming instantly, and FIG. 3B shows saturated crystals forming in the biocide composition, in accordance with an embodiment of the present invention;

FIG. 4 illustrates a comparison of crystal formation in biocide compositions, where the left composition has crystals formed without cavitation, and the right composition has crystals formed with cavitation by an ultrasonic rod, in accordance with an embodiment of the present invention; and FIGS. 5A, 5B, 5C, and 5D illustrate biocide compositions in different stages of crystal formation, where FIG. 5A shows saturated crystals initially added, FIG. 5B shows the crystal formation after fifteen minutes, FIG. 5C shows the crystal formation after four hours, and FIG. 5D shows the final composition with completed crystal formation, in accordance with an embodiment of the present invention.

Like reference numerals refer to like parts throughout the various views of the drawings.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the invention as depicted in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Specific dimensions and other physical characteristics relating to the embodiments disclosed herein are therefore not to be considered as limiting, unless the claims expressly state otherwise.

A honey based biocide composition 100 is referenced in FIGS. 1-5D. The biocide composition 100 provides an organic, food grade biocide that serves as an insecticide, moldicide, and fungicide. The biocide composition 100 consists of at least one constituent selected from the following ingredients: honey 102; acetylsalicylic acid 104; polysaccharide 106; guar gum 108; bee propolis 110; decylglucoside 112; and water 114. The crystallization of the honey 102 is central to the effectiveness of the biocide composition 100.

The ingredients that constitute the biocide composition 100 are combined with an acetylsalicylic acid 104 to provide a substantially organic, food grade biocide that may be used on plants and in proximity of food. In some embodiments, the ingredients may be combined to form an anti-biotic treatment on food, plants, people, animals, and inanimate surfaces. The purpose being chiefly to kill small insects and control contamination and the growth of molds, mildews, and fungus. The biocide composition 100 may take the form of saturated crystals 116 or a liquid for easy dispersion. Additionally, the formulation of the biocide composition 100 requires minimal costly ingredients or sophisticated laboratory equipment.

Those skilled in the art will recognize that the generally organic nature of the ingredients that make up the biocide composition 100 results in a safe, purely organic, environmentally friendly, and pesticide free biocide. Thus, the biocide composition 100 enables a process of keeping infestations under control without the use of dangerous chemicals. The composition 100 is formulated through generally known analytical chemistry that includes a series of mixing, heating, crystallization, dilutions, and finally liquefying into a usable form for dispersion. The biocide composition 100 kills undesirable insects and microorganisms rapidly and leaves a protective barrier behind when applied in a mist to the walls and surfaces of the plant.

One aspect of the honey 102 based biocide composition 100, comprises:

honey 102;
acetylsalicylic acid 104;
polysaccharide 106;
guar gum 108;
bee propolis 110;
decylglucoside 112; and
water 114.

In another aspect a method for preparing honey based biocide composition 100, the method comprising preparing a first solution by mixing acetylsalicylic acid 104 with honey 102, wherein the first solution is vibrated until crystals 116 are visible; preparing a second solution by mixing the crystals with the polysaccharide 106, wherein the second solution is blended into an aerated mixture to form supersaturated crystals 116, and then chilled; and preparing a third solution by mixing the supersaturated crystals 116 with acetylsalicylic acid 104, decylglucoside 112, and water 114, wherein the third solution is mixed with guar gum 108 and bee propolis 110 to prepare the biocide composition 100.

In another aspect, 325 milligrams of acetylsalicylic acid 104 is mixed with 1 pint of honey 102 to form the first solution.

In yet another aspect, the first solution is cooled at about 40° Fahrenheit for 15 minutes, and then returned to room temperature.

In another aspect, the first solution is vibrated at about 10,000 Hertz until crystals 116 are visible.

In another aspect, 2 ounces of the crystals 116 are mixed with one pint of the polysaccharide 106 to form the second solution.

In another aspect, the second solution is blended into an aerated mixture to form supersaturated crystals 116, and then chilled at about 40° Fahrenheit for 48 hours.

In another aspect, 2 ounces of the supersaturated crystals 116 are mixed with 320 milligrams of acetylsalicylic acid 104, ½ ounce of decylglucoside 112, and 1 gallon of water 114 to form the third solution.

In another aspect, the third solution is mixed with ⅛ ounce guar gum 108 and 1% concentration of bee propolis 110.

In yet another aspect, the guar gum 108 acts as a polysaccharide 106 to thicken the third solution so as to allow the mixture to concentrate and thereby allows for greater longevity after application.

In yet another aspect, by removing the decylglucoside 112 from the biocide composition 100 and adding twice the volume of the polysaccharides 106 in a citric acid results in an organic disinfectant for use directly on food.

In yet another aspect, the saturated crystal 116 form of the biocide 100 enhances the performance of the composition, wherein the biocide composition 100 comprising the decylglucoside 112 which acts as a surfactant to suspends the crystals 116 in an air-water solution, when applied to a surface the dilute crystals 116 will float along the surface of the surfactant and concentrate, i.e., super saturate, and become a chain of polymers that kills micro-organisms and small insects, further upon drying, the biocide composition 100 forms a protective surface of natural, long chain polymers and crystals 116 that prevent growth of molds, fungus, bacteria, and acts as a disinfectant and antibacterial agent.

In yet another aspect, supersaturated crystals may be formed separately, the supersaturated crystals consisting of:

isopropyl or ethyl alcohol;
acetylsalicylic acid 104;
water 114;
guar gum 108; and
bee propolis 110.

In yet another aspect, 0.25 grams of bee propolis 110 is dissolved in 5 milliliters of isopropyl or ethyl alcohol to form a first saturated solution.

In yet another aspect, 0.75 grams of acetylsalicylic acid 104 is dissolved in 5 milliliters of water 114 to form a second saturated solution.

In yet another aspect, the first saturated solution and the second saturated solution are mixed with 2 ounces of honey 102 and heated until dissolved into a third saturated solution.

In yet another aspect, the third saturated solution is mixed with a finished composition 100 of supersaturated crystals and a pint of honey 102.

One objective of the present invention is to provide an organic, food grade biocide that serves as an insecticide, fungicide, and moldicide.

Another objective is to provide a biocide composition 100 containing crystallized forms of honey 102 and other natural ingredients.

Another objective is to identify real honey and fake honey through observation of the crystals 116.

Another objective is to provide a biocide composition 100 that can be formulated with minimal expensive ingredients or analytical laboratory equipment.

Another objective is to provide a biocide composition 100 that can be used as a spray application to help fully spread the mixture over a wide area to facilitate the composition becomes active on contact with the air.

As shown in FIG. 1, the biocide composition 100 consists of at least one member from the following ingredients: honey 102; acetylsalicylic acid 104; polysaccharide 106; guar gum 108; bee propolis 110; decylglucoside 112; and water 114. The biocide composition 100 is formed through generally known analytical chemistry that includes a series of mixing, heating, crystallization, dilutions, and finally liquefying the biocide composition 100 into a usable form for dispersion. The crystallization of the honey 102 into a saturated crystal is an important concept for this process. A fully formed crystal 116 formed from the honey 102 is illustrated in FIG. 2.

In the formulation of the biocide composition 100, about 325 milligrams of acetylsalicylic acid 104 is mixed with one pint of honey 102 to form a first solution. In some embodiments, a natural, organic honey 102 may be used. The mixture forming the first solution may be performed at about 115° Fahrenheit to compensate for the generally low viscosity of honey 102.

In some embodiments, the first solution is cooled at about 40° Fahrenheit for 15 minutes, and then returned to room temperature. The first solution may then be placed in a dark room at room temperature for further processing. The mixing and cooling process may be performed in a container 118, such as a glass jar. Next, the formation of a plurality of crystals 116 is desirable. Those skilled in the art will recognize that when ingredients are combined to form the biocide composition 100, crystallization is necessary for optimal performance. Without crystallizing there is no active composition and the solution is minimally effective. When super saturation and pre-crystallization is performed, the first solution can be diluted to a greater amount and remain effective.

The reason that the crystals 116 enhance the performance of the composition 100 is because the action of the decylglucoside 112 (surfactant), which suspends the crystals 116 in an air-water solution that remains dilute until it comes into contact with a surface. Upon contact with the surface the dilute crystals 116 will float along the slippery surface of the surfactant and concentrate, i.e., super saturate, and become a chain of polymers that kills micro-organisms and small insects. Upon drying, the biocide composition 100 forms natural, long chain polymers and crystals 116 that prevent the growth of molds, fungus, bacteria, and acts as a disinfectant and antibacterial agent. This protective surface is formed in minutes and becomes water resistant after about an hour. After activation with the air the products half-life is approximately one week. In one embodiment, re-application within a week extends product effectiveness without causing build up or clogging of a plant leaf stoma.

Figure 1:
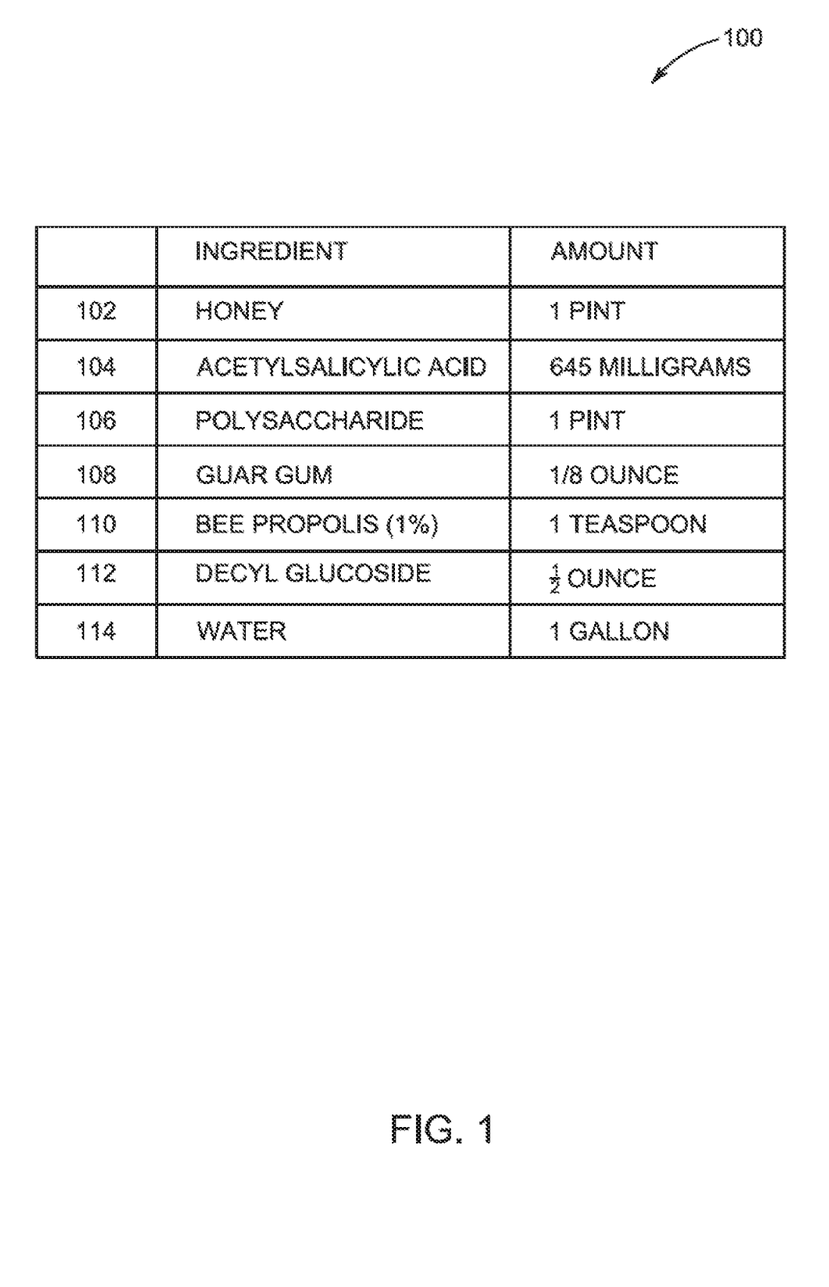
Figure 2:
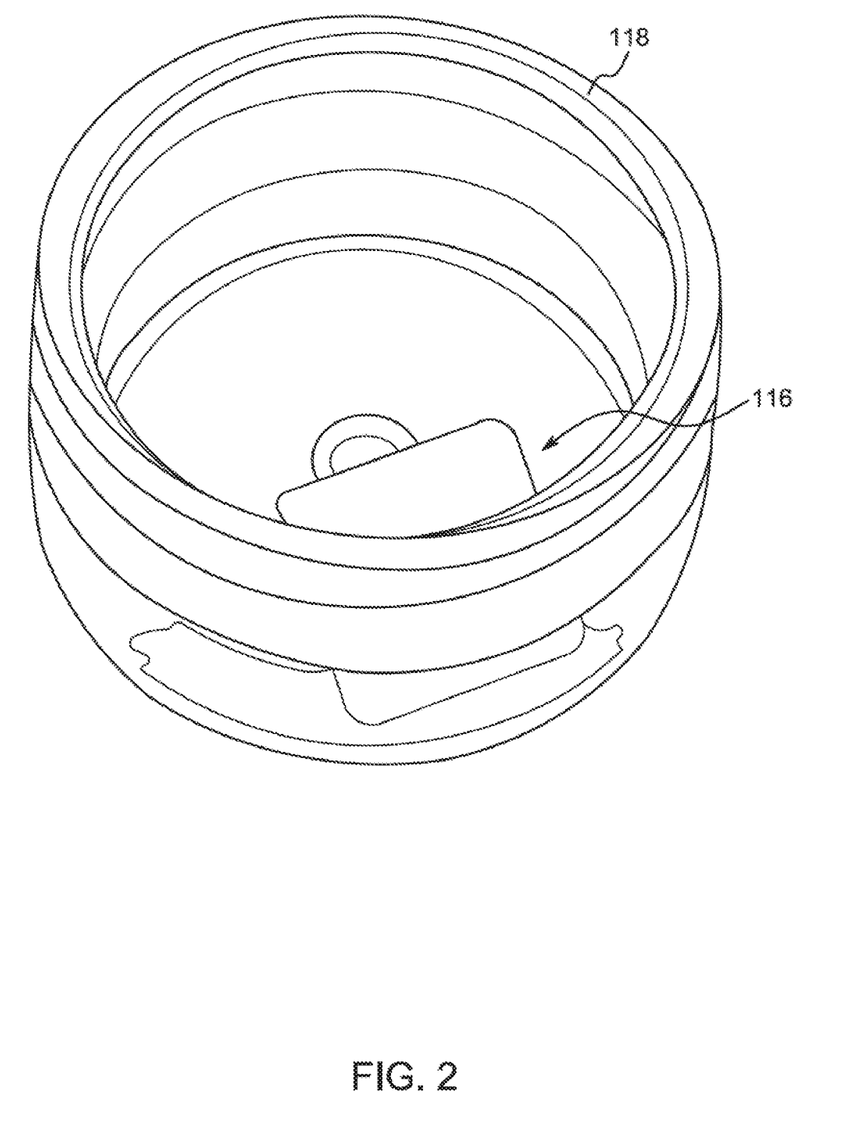
Figure 3A:
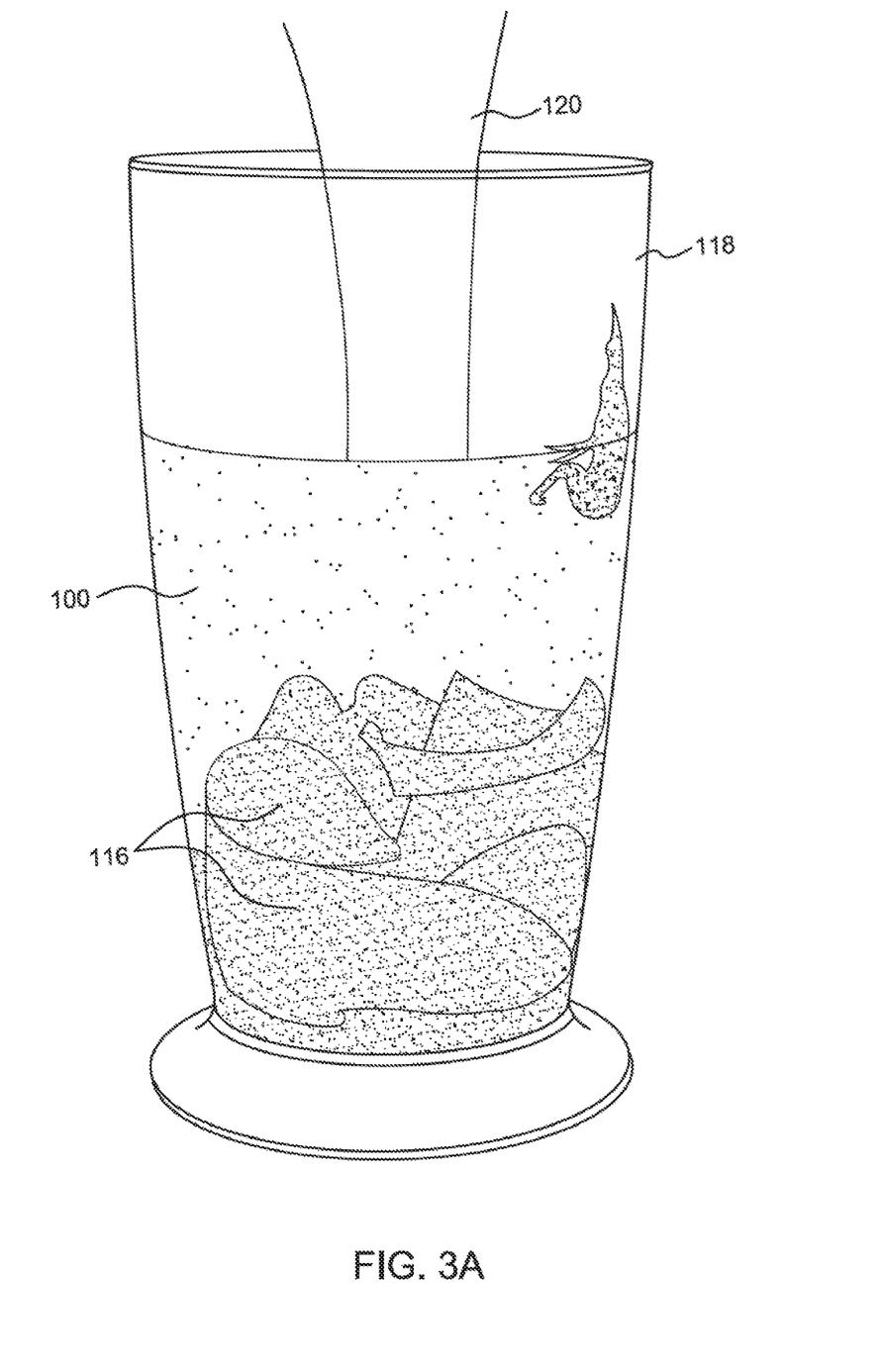
Figure 3B:
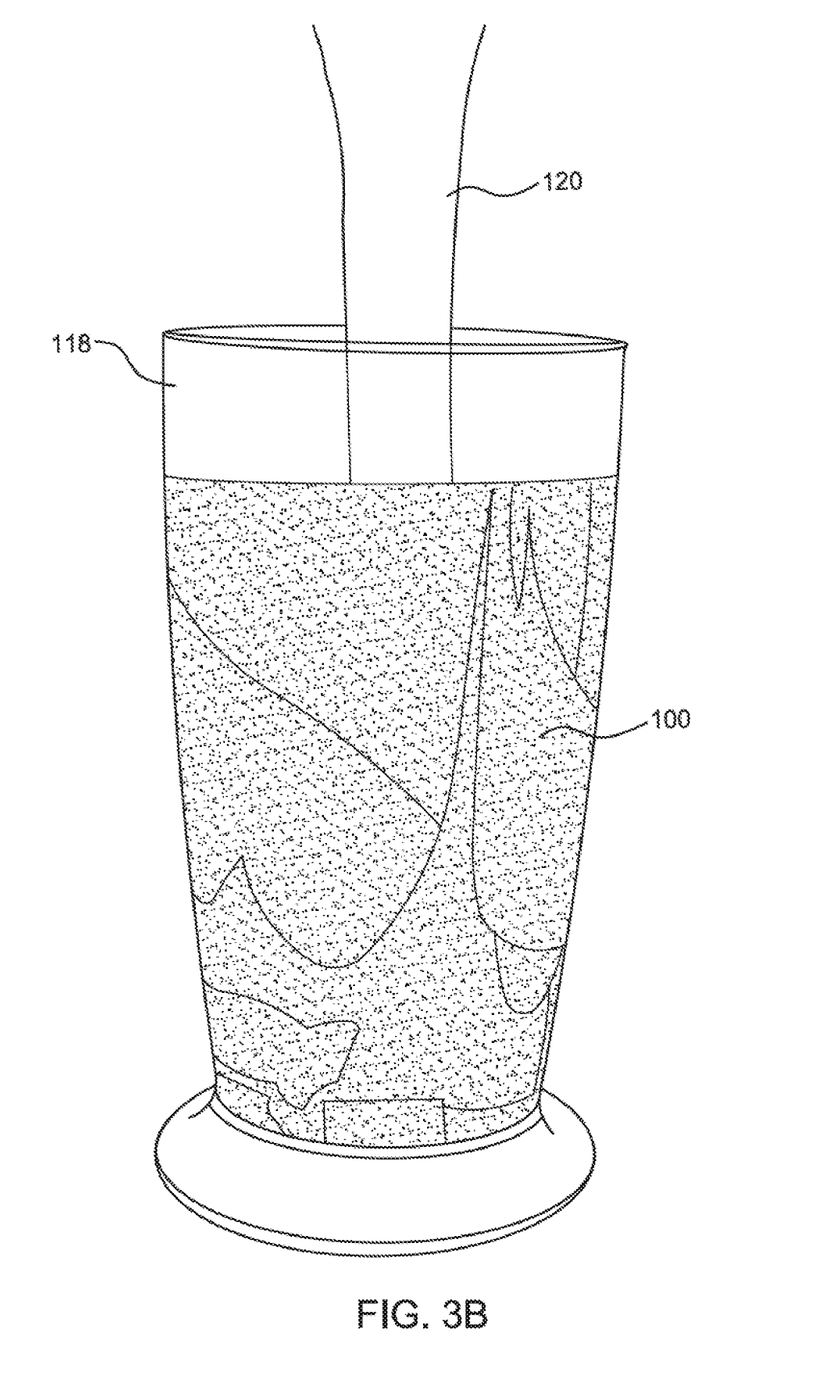
Figure 4:
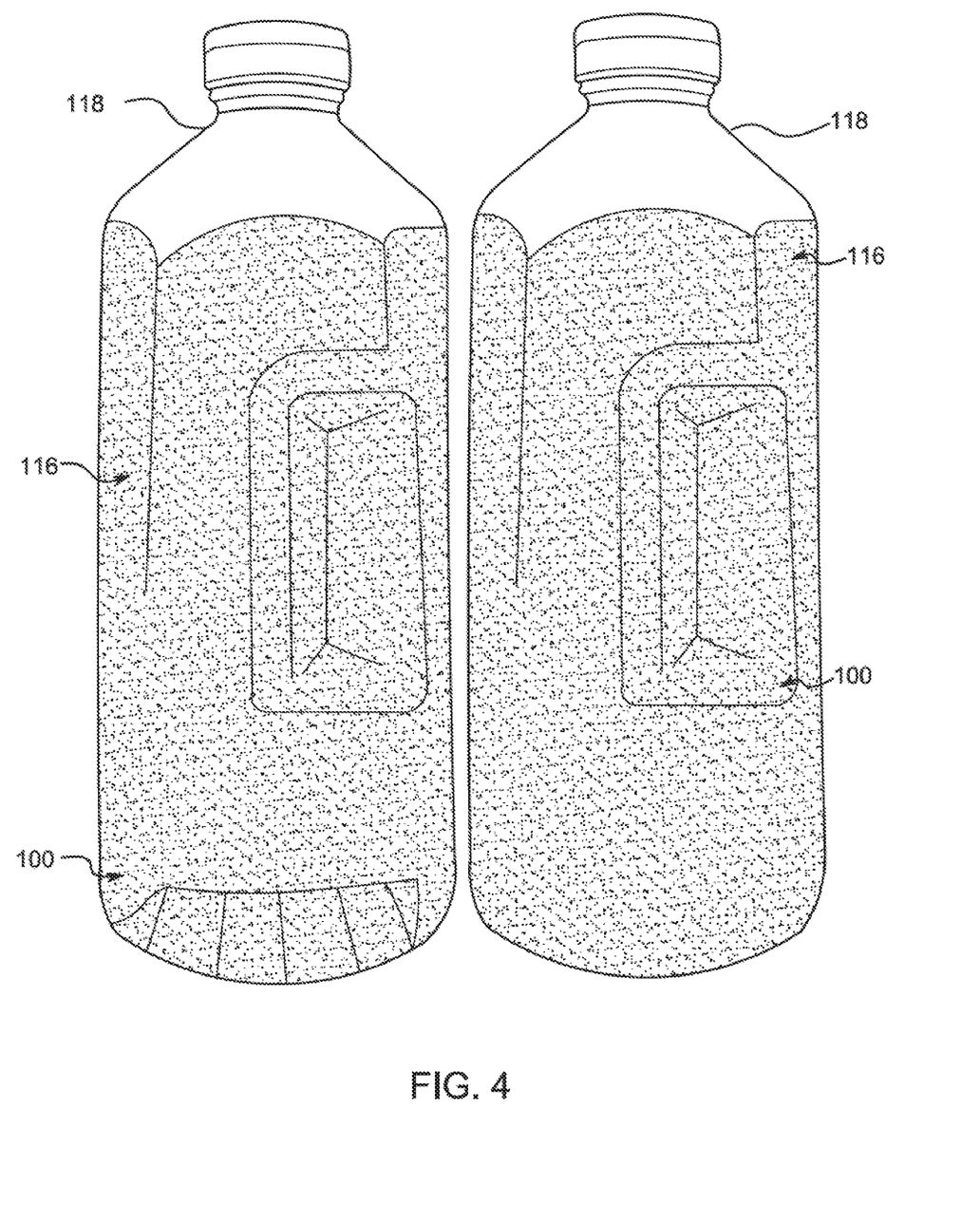
Figure 5A:
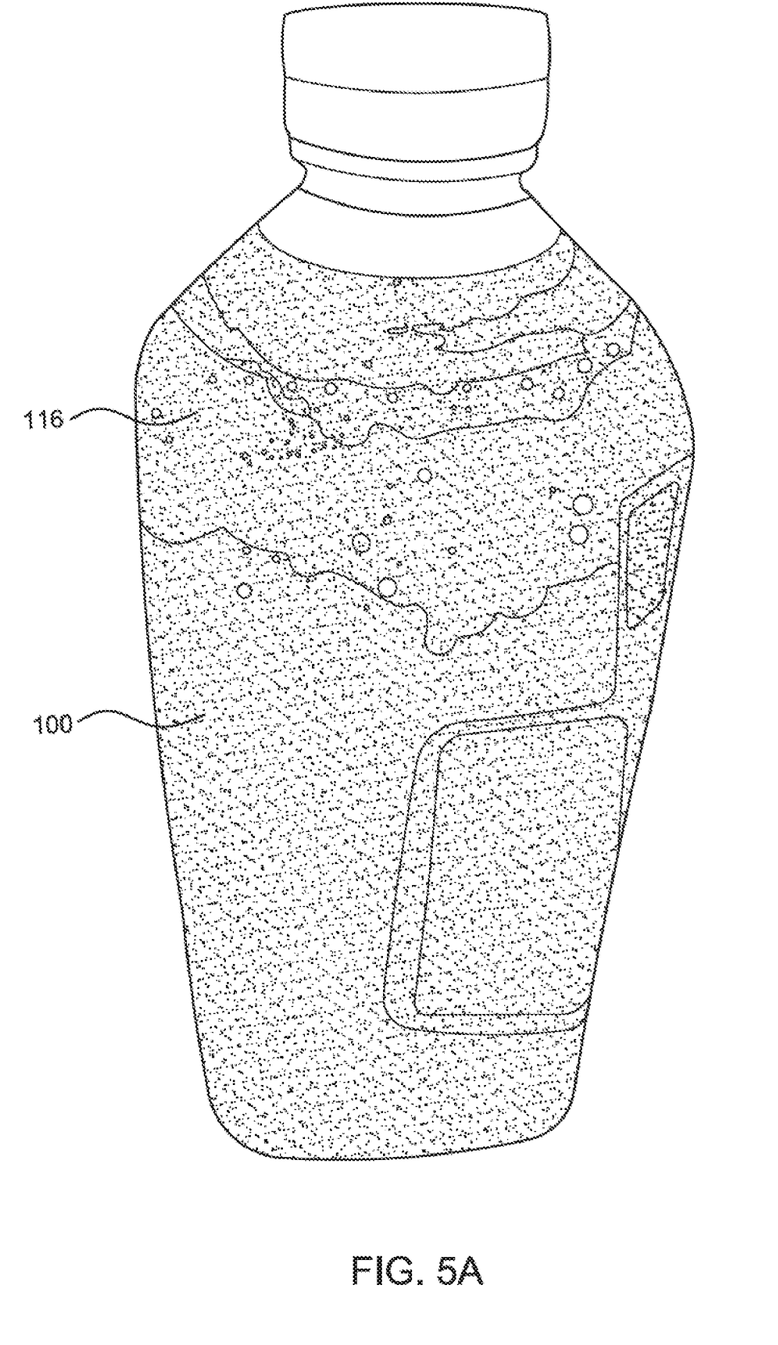
Figure 5B:
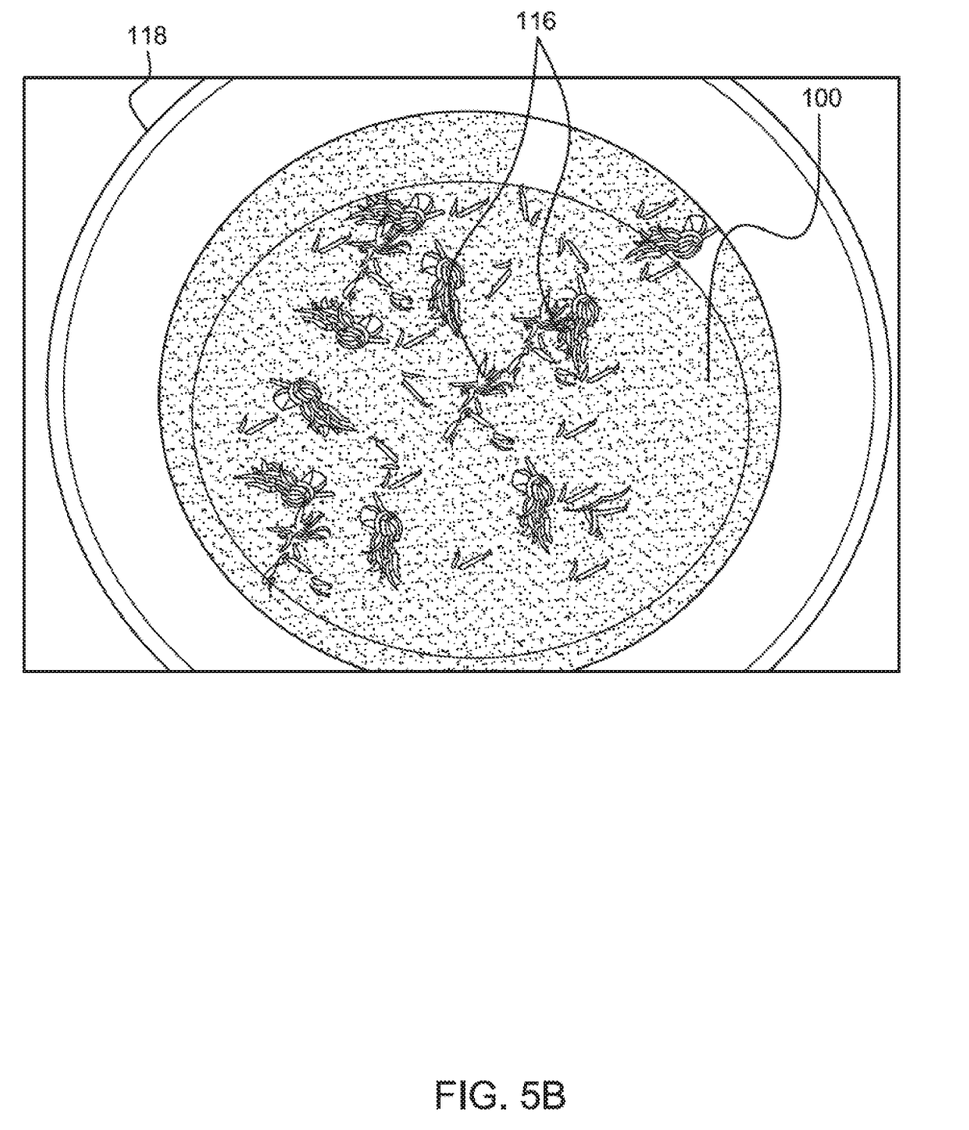
Figure 5C:
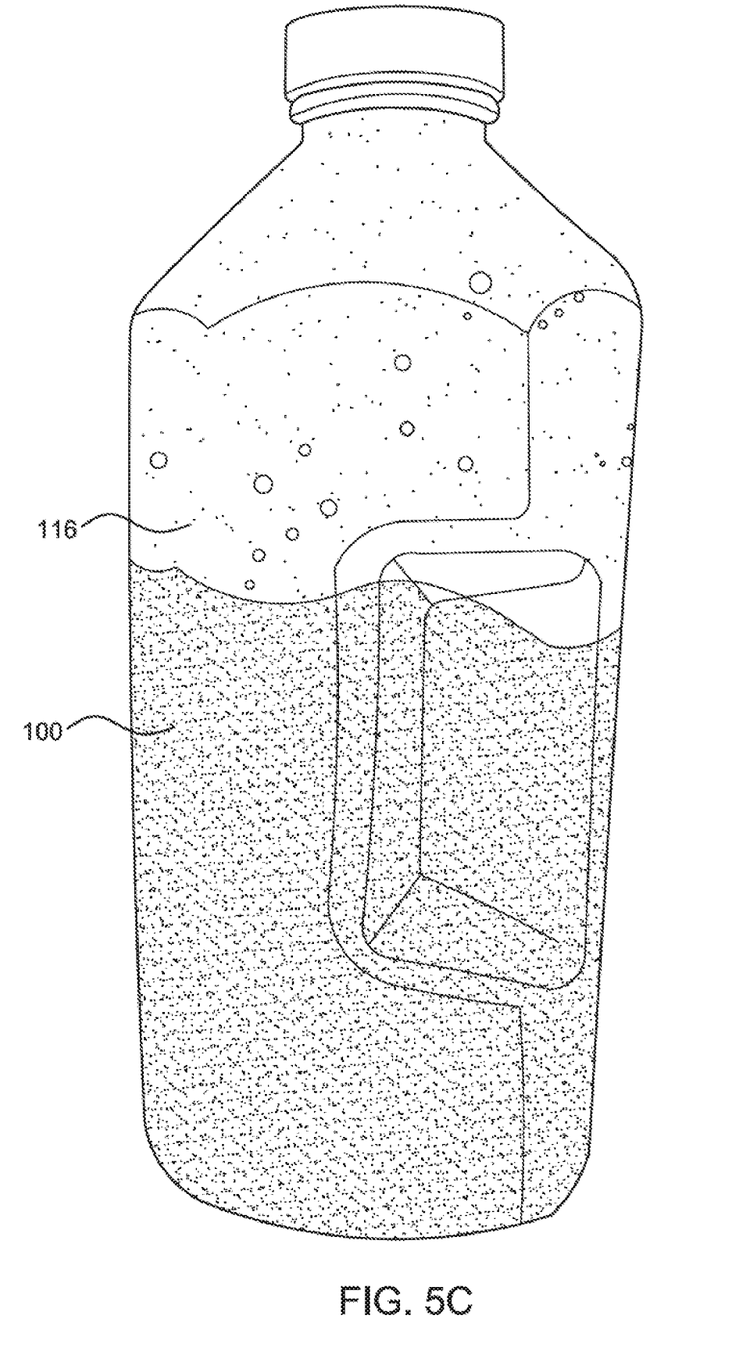
Figure 5D:
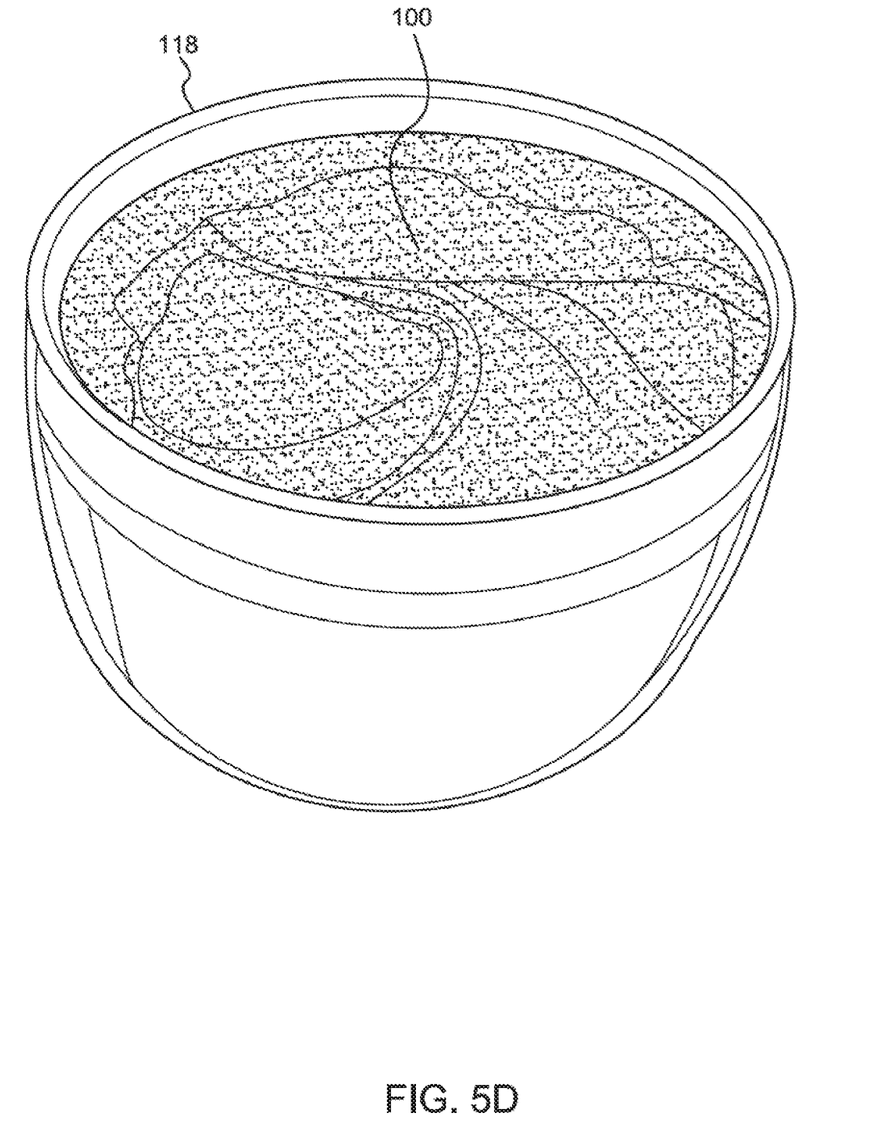

Those skilled in the art will also recognize that in the electronics industry, crystals 116 are grown in silicon to make transistors and microchips. The action of crystals 116 to hold and release their charge is known as the piezoelectric effect. The inventor asserts that the anti-biotic, anti-fungal, anti-microorganism abilities of the biocide composition 100 are a direct result of this effect. Specifically, as the crystals 116 form, they gain a strong bond through an electric charge. When the crystals 116 again reform as they surround the insect or microorganism they again gain this charge, essentially electrocuting the insect or microorganism. Furthermore, once mixed with water 114 the composition 100 becomes air activated and should only be kept in a pressure vessel. The pressure developed may be maintained at 3 psi or less, even when shaken.

Thus, the desired crystallization in the first solution is formed as a polar solvent reaches concentrations rich enough to crystallize in the presence of a nucleation site formed though a shock or chemical change causing an endothermic reaction. In one embodiment, the shock may include rapidly vibrating or oscillating the first solution. For example, the first solution is vibrated at about 10,000 Hertz until crystals 116 are visible. In one embodiment referenced in FIG. 3A, powerful vibrations are generated by an ultrasonic rod 120, or vibrating head. In one embodiment, the ultrasonic rod 120 is submerged into the container 118 at a frequency of 10,000 Hz. The volume or amplitude may, however, be adjusted until visible crystals 116 are seen forming at the site. This may be done through shock or cavitations. In one embodiment, the ultrasonic rod 120 is moved throughout the first solution in the container 118 to spread the formed crystals 116. There is also a ratio of temperature and vibration; whereas the colder the contents the greater the formation of crystals 116.

As illustrated in FIG. 3B, the container 118 may be rotated every twelve hours to allow the crystals 116 to move and fully integrate throughout the first solution. If necessary, the first solution may be allowed to warm slightly before rotation to allow movement of crystals 116 throughout. The more air that is allowed in the first solution, the more nucleation sites and the smaller the crystals 116. Those skilled in the art will recognize that it is preferable that the crystals 116 be large and grown in as great an amount as possible. This formulation process is efficacious for not only proving that the honey 102 is pure (fake honey will not crystallize), but the formulation process also forces rapid re-crystallization after dilution in the following process described below.

FIG. 4 illustrates a comparison of crystal formation in the biocide composition 100, where the left biocide composition 100 has crystals 116 formed without cavitations from the ultrasonic rod 120, and the right biocide composition 100 has crystals 116 formed with cavitations by the ultrasonic rod 120. FIGS. 5A, 5B, 5C, and 5D illustrate different biocide compositions 100 at different stages of crystal 116 formation. For example, FIG. 5A shows saturated crystals 116 initially added, FIG. 5B shows the crystal 116 formation after fifteen minutes, FIG. 5C shows the crystal 116 formation after four hours, and FIG. 5D shows the final composition 100 with completed crystal 116 formation.

In some embodiments, after at least two days of sitting, two ounces of the formed crystals 116 are mixed with one pint of a polysaccharide 106 to form a second solution. The second solution is blended into an aerated mixture to form supersaturated crystals, and then chilled at about 40° Fahrenheit for 48 hours. It is significant to note that these supersaturated crystals may also be formed separately, as described below. A next step in the process includes mixing two ounces of the supersaturated crystals with 320 milligrams of acetylsalicylic acid 104, ½ ounce of decylglucoside 112 (surfactant), and one gallon of water 114 to form a third solution.

In some embodiments, the third solution is mixed with ⅛ ounce guar gum 108 and 1% concentration of bee propolis 110. The guar gum 108, which is a polysaccharide 106 itself, serves to thicken the third solution. Thickening the third solution in this way allows the mixture to concentrate and allows for greater longevity after application. The addition of bee propolis 110 at 1% acts in synergy with the honey 102 and increases the ability to provide the insecticide, moldicide, or fungicide functionality.

The supersaturated crystals may be formed separately for combining into the biocide composition 100, rather than formed during formulation of the biocide composition 100. This segregated formulation of super crystals may be useful for creating an accessible stockpile of base ingredients for the biocide composition 100. In one embodiment, the supersaturated crystals 116 consisting of: isopropyl or ethyl alcohol; acetylsalicylic acid 104; water 114; guar gum 108; and bee propolis 110.

An initial step in formulating the saturated crystals involves dissolving 0.25 grams of bee propolis 110 in 5 milliliters of isopropyl or ethyl alcohol to form a first saturated solution. Next, 0.75 grams of acetylsalicylic acid 104 is dissolved in 5 milliliters of water 114 to form a second saturated solution. Next, the first saturated solution and the second saturated solution are mixed with two ounces of honey 102 and heated until dissolved into a third saturated solution. Finally, the third saturated solution is mixed with a finished solution of supersaturated crystals 116 and a pint of honey 102.

The biocide composition 100 is sufficiently flexible in that the ingredients and mixing conditions can be slightly varied to create a more specific biocide composition 100 (FIG. 1). Honey 102 remains, however, the core ingredient in any alternative embodiment of the biocide composition 100. These alternative embodiments are described below. For example, a composition 100 that is more effective as a fungicide than an insecticide. In one example, the removal of the decylglucoside 112 from the ingredients, and the addition of twice the volume (or 4 ounces) of polysaccharides 106 in a citric acid results in an organic disinfectant for use directly on food. This formulation is effective for killing *Salmonella* and also acts as an anti-biotic.

In another example, by increasing the decylglucoside 112 from ½ ounce to one ounce, the preparation becomes an organic disinfecting cleaner safe for use on inanimate surfaces around food. Additionally, through the addition of citric acids or citric extracts, the anti-bacterial effects become profound and by elimination of the decylglucoside 112 the composition 100 becomes an effective spray for use on food to kill *E-coli, Salmonella* and acts as an effective anti-bacterial agent. In yet another alternative embodiment, adjusting the levels of crystals 116 to decylglucoside 112 and the nutritive properties to plants is apparent. Additional preparations may include concentrates. These concentrates may be made strictly using pure large crystals 116 wrapped in dry powdered surfactant and the acetylsalicylic acid 104. One such preparation could be a dry concentrate, mixed at about a 25 to 1 ratio.

In some embodiments, all the constituent ingredients in the biocide composition 100 are water soluble or are polar solvent with a completed mixture pH of about 6.9. The natural color of the composition 100 is a pale golden yellow (FIG. 3A). In one embodiment, a blue dye (FD&C 1) may be added to give product a pale green tint. The added surfactant gives the composition 100 a slight soapy smell and taste that is associated with a clean smell of flowers. The product shelf life of the container 118 in which the composition 100 is stored is indefinite as no organisms will grow in this mixture and the contents do not react or break down. Furthermore, the container 118 maintains a slightly small internal pressure that regulates the surface activation with the air.

In use, the biocide composition 100 is best used in a spray application to help fully spread the mixture over a wide area, especially since the composition 100 becomes active on contact with the air. It is best used as a preventative spray once a week. The composition 100 contains only food safe, organic ingredients that together act as an anti-bacterial 3 in 1 spray (fungicide, moldicide, insecticide) on all types of plants, trees and surfaces around food. As a spray of fog, this can be used as a treatment for ridding the home of mold and fungal invasions, directly on surfaces. In one embodiment, after all the mold is removed a preparation of bee propolis 110 of 1% dissolved in water 114 is applied to exposed surfaces to prevent the return of any molds or mildew.

Those skilled in the art, in light of the present teachings, will recognize that the action and process of preparing the biocide composition 100 is distinguished from the existing prior arts. The actions and processes of ingredients that can reach super saturation levels are known to create an endothermic reaction when crystallization occurs. It is in the nature of using the action of super saturation of the extract to kill living cells through the action of bursting their cellular walls (hyper-osmolar reaction). This action of crystal 116 formations and cell wall bursting is similar to exposing the organism to temperatures −25° Fahrenheit.

When introduced into a weak alcohol and water solution the extract disperses into small clumps remaining super saturated in action and dispersed in suspension up to concentration of two table spoons extract per gallon. When in suspension of this solution the half-life of the anti-microbial action is indefinite (15 years at least). Advanced testing on the safety of the biocide composition 100 found that it is as safe as any food grade carbohydrate in super saturation and is safe around children, animals and plants; is non-allergenic, and legally considered food grade, safe if ingested and neutral in pH requiring only water 114 to flush from eyes.

Those skilled in the art will recognize that in a test group of 10,000 university students there were no reports of any allergic or skin reactions, and no complaints of illness or side effects when the biocide composition 100 was ingested. Furthermore, skin allergy puncture tests (not shown) showed a complete absence of pain or redness on a test group of 1,000 college students. Furthermore, concentrations of up to 100% were tested on all subjects including animals and plants. When sprayed on plants in the higher concentrations from 25% -100% the stoma, or breathing holes in plant leaves were blocked by the viscosity of the extract. If left on, the leaves began to react as they would in the presence of anything with a high viscosity and clog the respiratory process. Because the extract of the biocide composition 100 is water soluble it washes off easily. It was also found that when the extract is applied in concentrations from 1% up that this action works on small insects of up to ¼ ounce in weight, killing the smaller insects within a minute; whereas larger insects would require higher concentrations to be killed.

These and other advantages of the invention will be further understood and appreciated by those skilled in the art by reference to the following written specification, claims and appended drawings.

Because many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What I claim is:

1. A honey based biocide composition, the composition comprising:
- honey;
- acetylsalicylic acid;
- polysaccharide;
- guar gum;
- bee propolis;
- decylglucoside; and
- water.

2. The biocide composition of claim 1, wherein the biocide composition containing crystallized forms of honey and further the composition provides an organic, food grade biocide that serves as an insecticide, moldicide, and fungicide.

3. The biocide composition of claim 1, wherein the biocide composition consisting of 1 pint of honey, 645 milligrams of acetylsalicylic acid, 1 pint of polysaccharide, ⅛ ounce of guar gum, one teaspoon of 1% concentration of bee propolis, ½ ounce of decylglucoside and 1 gallon of water.

4. The biocide composition of claim 1, wherein the biocide composition is used as a spray application to help fully spread the mixture over a wide area to facilitate the composition becomes active on contact with the air.

5. The biocide composition of claim 1, wherein removing the decylglucoside from the biocide composition and adding twice the volume of the polysaccharides in a citric acid results in an organic disinfectant for use directly on food.

6. The biocide composition of claim 1, wherein the composition once mixed with water becomes air activated and thus kept in a pressure vessel maintained at 3 psi or less.

7. The biocide composition of claim 1, wherein the composition has a pH of about 6.9.

8. A honey based biocide composition prepared by a process comprising the steps of:
- preparing a first solution by mixing acetylsalicylic acid with honey;
- vibrating the first solution until crystals are visible;
- preparing a second solution by mixing the crystals with a polysaccharide;
- preparing supersaturated crystals by blending the second solution under conditions to provide a sufficiently aerated mixture thereby forming the saturated crystals, and then chilling the supersaturated crystals;
- preparing a third solution by mixing the supersaturated crystals with acetylsalicylic acid, decylglucoside, and water; and
- mixing the third solution, guar gum, and bee propolis, in amounts effective to prepare the biocide composition.

9. The biocide composition of claim 8, wherein the first solution is prepared by mixing about 325 milligrams of acetylsalicylic acid with about 1 pint of honey, and wherein the first solution is cooled to about 40° Fahrenheit for at least 15 minutes and the further cooled to room temperature.

10. The biocide composition of claim 8, wherein the vibrating of the first solution comprises vibrating at about 10,000 Hz until the crystals are visible.

11. The biocide composition of claim 8, wherein preparing the second solution comprises mixing about 2 ounces of the crystals with one pint of the polysaccharide.

12. The biocide composition of claim 8, wherein preparing the supersaturated crystals comprises mixing at least one of the following: isopropanol, ethanol, acetylsalicylic acid, water, guar gum, and bee propolis.

13. The biocide composition of claim 8, wherein the third solution is prepared by mixing about 2 ounces of the supersaturated crystals with about 320 milligrams of acetylsalicylic acid, ½ ounce of decylglucoside, and 1 gallon of water, further the third solution is mixed with ⅛ ounce guar gum and one teaspoon of a 1% (w/v) concentration of bee propolis.

14. The biocide composition of claim 8, wherein the guar gum thickens the third solution and thereby allows for greater longevity of the biocide activity after application.

15. The biocide composition of claim 8, wherein in the biocide composition the decylglucoside and supersaturated crystals are present in amounts sufficient to (i) kill micro-organisms and small insects in solution, or (ii) inhibit growth of molds, fungi, and bacteria.

16. A honey based biocide composition prepared by a process comprising the steps of:
preparing a first solution by mixing about 325 milligrams of acetylsalicylic acid with about 1 pint of honey;
vibrating the first solution at about 10,000 Hz until crystals are visible;
preparing a second solution by mixing about 2 ounces of the crystals with one pint of a polysaccharide;
preparing supersaturated crystals by blending the second solution under conditions to provide a sufficiently aerated mixture thereby forming the supersaturated crystals, and then chilling the supersaturated crystals at about 40° Fahrenheit for 48 hours;
preparing a third solution by mixing about 2 ounces of the supersaturated crystals with about 320 milligrams of acetylsalicylic acid, about ½ ounce of decyglucoside, and 1 gallon of water; and
mixing the third solution, ⅛ ounce guar gum, and one teaspoon of a 1% (w/v) concentration of bee propolis, the amounts thereof effective to prepare the biocide composition,
wherein in the biocide composition the decylglucoside and supersaturated crystals are present in amounts sufficient to (i) kill micro-organisms and small insects in solution, or (ii) inhibit growth of molds, fungi, and bacteria.

17. The biocide of claim 16, wherein the first solution is cooled to about 40° Fahrenheit for 15 minutes, and then further cooled to room temperature.

18. The biocide of claim 16, wherein preparing the supersaturated crystals comprises mixing at least one of the following: isopropanol, ethanol, acetylsalicylic acid, water, guar gum, and bee propolis.

19. The biocide of claim 16, wherein the biocide composition is an organic, food-grade biocide, useful as an insecticide, a moldicide and a fungicide.

20. The biocide of claim 19, wherein the biocide composition is a sprayable composition.

* * * * *